(12) United States Patent
Loh et al.

(10) Patent No.: US 12,402,606 B2
(45) Date of Patent: Sep. 2, 2025

(54) HEALTH MONITORING SYSTEM AND DEVICE FOR LIVESTOCK

(71) Applicant: PTS Technologies Pte Ltd, Singapore (SG)

(72) Inventors: Albert Kim Huat Loh, Singapore (SG); Lwin Aye Han, Singapore (SG)

(73) Assignee: PTS Technologies Pte Ltd, Singapore (SG)

( * ) Notice: Subject to any disclaimer, the term of this patent is extended or adjusted under 35 U.S.C. 154(b) by 0 days.

(21) Appl. No.: 18/274,037

(22) PCT Filed: Jan. 29, 2021

(86) PCT No.: PCT/SG2021/050039
§ 371 (c)(1),
(2) Date: Jul. 25, 2023

(87) PCT Pub. No.: WO2022/164382
PCT Pub. Date: Aug. 4, 2022

(65) Prior Publication Data
US 2024/0423168 A1    Dec. 26, 2024

(51) Int. Cl.
*G08B 23/00* (2006.01)
*A01K 29/00* (2006.01)
*A61B 5/00* (2006.01)

(52) U.S. Cl.
CPC .......... *A01K 29/005* (2013.01); *A61B 5/0002* (2013.01); *A61B 2503/40* (2013.01)

(58) Field of Classification Search
CPC .. A01K 29/005; A61B 5/0002; A61B 2503/40
See application file for complete search history.

(56) References Cited

U.S. PATENT DOCUMENTS

| | | | | |
|---|---|---|---|---|
| 5,363,425 A | * | 11/1994 | Mufti | H04Q 3/625 |
| | | | | 455/433 |
| 5,482,008 A | * | 1/1996 | Stafford | A01K 11/007 |
| | | | | 128/899 |

(Continued)

FOREIGN PATENT DOCUMENTS

| | | |
|---|---|---|
| WO | 2017127913 A1 | 8/2017 |
| WO | 2019089456 A1 | 5/2019 |

OTHER PUBLICATIONS

International Search Report and Written Opinion of International Searching Authority with mailing date of Apr. 1, 2021 for PCT/SG2021/050039.

*Primary Examiner* — Quang Pham
(74) *Attorney, Agent, or Firm* — JCIP; Joseph G. Chu (57) ABSTRACT

The present disclosure generally relates to a monitoring device (100) for remotely monitoring health of a young livestock animal (10), the device (100) comprising: an elongated body (110) within predefined dimensional limits; and a set of electronic components housed within the elongated body (110), the electronic components comprising: a temperature sensor for measuring body temperature of the young livestock animal (10); a computer processor for processing the measured temperature into temperature data; and a wireless communications component for transmitting the temperature data to a remote computer device (210) for processing to monitor the health of the young livestock animal (10), wherein the predefined dimensional limits of the elongated body (110) enable the monitoring device (100) to be orally administrable into the young livestock animal (10) and to remain inside its stomach (12) without being excreted.

17 Claims, 3 Drawing Sheets

(56) References Cited

U.S. PATENT DOCUMENTS

| | | | | |
|---|---|---|---|---|
| 6,236,318 B1* | 5/2001 | Yang | A61D 17/002 | 600/549 |
| 8,989,053 B1* | 3/2015 | Skaaksrud | G05D 1/81 | 370/255 |
| 10,231,644 B2* | 3/2019 | Rettedal | A61B 5/4238 | |
| 10,306,868 B2* | 6/2019 | Rettedal | A01K 11/008 | |
| 10,390,515 B2* | 8/2019 | Bancroft | H01Q 21/29 | |
| 10,548,509 B2* | 2/2020 | Rettedal | A61D 7/00 | |
| 2002/0010390 A1* | 1/2002 | Guice | G16H 50/20 | 600/300 |
| 2004/0143182 A1* | 7/2004 | Kucera | A61B 5/073 | 600/424 |
| 2005/0134452 A1* | 6/2005 | Smith | A61B 5/1112 | 600/300 |
| 2007/0088194 A1* | 4/2007 | Tahar | A61B 5/0031 | 600/102 |
| 2007/0187513 A1* | 8/2007 | Marin Palacios | G01R 33/14 | 235/462.37 |
| 2008/0236500 A1* | 10/2008 | Hodges | A01K 11/007 | 340/573.3 |
| 2009/0048498 A1* | 2/2009 | Riskey | A61B 5/4238 | 600/302 |
| 2009/0182207 A1* | 7/2009 | Riskey | A61B 5/1124 | 600/587 |
| 2009/0187392 A1* | 7/2009 | Riskey | A61B 5/4238 | 703/11 |
| 2010/0245052 A1* | 9/2010 | Kitayoshi | H04B 5/48 | 340/10.4 |
| 2012/0119346 A1* | 5/2012 | Im | H01L 23/42 | 257/E23.18 |
| 2015/0031963 A1* | 1/2015 | Wright | A61B 5/6871 | 600/301 |
| 2015/0230727 A1* | 8/2015 | Mallinson | A61B 5/01 | 600/301 |
| 2016/0120154 A1* | 5/2016 | Hill | A01K 11/008 | 340/573.3 |
| 2016/0249083 A1* | 8/2016 | Okimoto | H04N 21/2543 | |
| 2017/0007352 A1* | 1/2017 | King | A61B 5/064 | |
| 2017/0091783 A1* | 3/2017 | Mancevski | G06K 19/06028 | |
| 2017/0215763 A1* | 8/2017 | Helfrich | A61B 5/073 | |
| 2017/0340243 A1* | 11/2017 | Jain | A61B 5/0084 | |
| 2017/0354121 A1* | 12/2017 | Fraser | G06M 11/00 | |
| 2018/0005101 A1* | 1/2018 | Kouki | G06K 19/0701 | |
| 2018/0103879 A1* | 4/2018 | Masciotti | A61B 5/0075 | |
| 2018/0310885 A1* | 11/2018 | Kim | G16H 40/67 | |
| 2019/0200896 A1* | 7/2019 | Rettedal | A61B 5/073 | |
| 2020/0375148 A1* | 12/2020 | Magazzù | A61B 5/0002 | |
| 2022/0202549 A1* | 6/2022 | Stevenson | A61C 19/063 | |
| 2022/0361444 A1* | 11/2022 | Cannon | A01K 29/005 | |

* cited by examiner

Figure 7

HEALTH MONITORING SYSTEM AND DEVICE FOR LIVESTOCK

TECHNICAL FIELD

The present disclosure generally relates to a health monitoring system and device for livestock. More particularly, the present disclosure describes various embodiments of a monitoring device for remotely monitoring health of a livestock animal, as well as a system for monitoring the health of livestock animals using the monitoring devices.

BACKGROUND

Livestock are reared in farms for various purposes including producing food for human consumption. A farm's productivity from livestock is dependent on their health and it is important to be able to monitoring their health constantly. Body temperature monitoring is one of the most effective ways of evaluating the health of livestock animals to ensure they are not compromised by infection or disease. Farmers traditionally use thermometers to measure body temperature of each of their livestock animals rectally. However, this labour-intensive manual measuring of body temperature on the farm is very tedious and inefficient.

Therefore, in order to address or alleviate at least one of the aforementioned problems and/or disadvantages, there is a need to provide an improved monitoring system and device for livestock.

SUMMARY

According to a first aspect of the present disclosure, there is a monitoring device for remotely monitoring health of a young livestock animal, the device comprising:
 an elongated body within predefined dimensional limits; and
 a set of electronic components housed within the elongated body, the electronic components comprising:
  a temperature sensor for measuring body temperature of the young livestock animal;
  a computer processor for processing the measured temperature into temperature data; and
  a wireless communications component for transmitting the temperature data to a remote computer device for processing to monitor the health of the young livestock animal,
 wherein the predefined dimensional limits of the elongated body enable the monitoring device to be orally administrable into the young livestock animal and to remain inside its stomach without being excreted.

According to a second aspect of the present disclosure, there is a monitoring system for remotely monitoring health of livestock animals comprising young livestock animals, the monitoring system comprising:
 a set of monitoring devices;
 a remote computer device communicative with the monitoring devices; and
 each monitoring device residing in a stomach of a respective livestock animal, the monitoring device comprising:
  an elongated body within predefined dimensional limits that enable the monitoring device to remain inside its stomach without being excreted and to be orally administered into the stomach of a young livestock animal;
  a set of electronic components housed within the body, the electronic components comprising:
   a temperature sensor for measuring temperature of the livestock animal;
   a computer processor for processing the measured temperatures into temperature data; and
   a wireless communications component for transmitting the temperature data to the remote computer device,
 wherein the remote computer device is configured for processing the temperature data to monitor the health of the livestock animals.

A monitoring system and device for livestock according to the present disclosure are thus disclosed herein. Various features, aspects, and advantages of the present disclosure will become more apparent from the following detailed description of the embodiments of the present disclosure, by way of non-limiting examples only, along with the accompanying drawings.

DETAILED DESCRIPTION

For purposes of brevity and clarity, descriptions of embodiments of the present disclosure are directed to a monitoring system and device for livestock, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognised by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

In embodiments of the present disclosure, depiction of a given element or consideration or use of a particular element number in a particular figure or a reference thereto in corresponding descriptive material can encompass the same, an equivalent, or an analogous element or element number identified in another figure or descriptive material associated therewith.

References to "an embodiment/example", "another embodiment/example", "some embodiments/examples", "some other embodiments/examples", and so on, indicate that the embodiment(s)/example(s) so described may include a particular feature, structure, characteristic, property, element, or limitation, but that not every embodiment/example necessarily includes that particular feature, structure, characteristic, property, element or limitation. Furthermore, repeated use of the phrase "in an embodiment/example" or "in another embodiment/example" does not necessarily refer to the same embodiment/example.

The terms "comprising", "including", "having", and the like do not exclude the presence of other features/elements/steps than those listed in an embodiment. Recitation of certain features/elements/steps in mutually different embodiments does not indicate that a combination of these features/elements/steps cannot be used in an embodiment.

As used herein, the terms "a" and "an" are defined as one or more than one. The use of "/" in a figure or associated text is understood to mean "and/or" unless otherwise indicated. The term "set" is defined as a non-empty finite organisation of elements that mathematically exhibits a cardinality of at least one (e.g. a set as defined herein can correspond to a unit, singlet, or single-element set, or a multiple-element set), in accordance with known mathematical definitions.

The present disclosure describes remote health monitoring of livestock. Livestock may be defined as domesticated animals raised in an agricultural setting to produce labour and commodities, such as food (e.g. meat, eggs, and milk) and materials (e.g. fur and wool). The United States defines the term "livestock" as including cattle, sheep, horses, goats, and other domestic animals ordinarily raised or used on the farm. This term can sometimes be used to refer solely to animals that are bred for consumption, while other times it may refer only to farmed ruminants, such as cattle and goats. Ruminants may be defined as herbivorous mammals that are able to acquire nutrients from food by fermenting it in a specialized stomach prior to digestion. The ruminant stomach is a multi-chambered organ and usually has four separate chambers—rumen, reticulum, omasum, and abomasum. The rumen and reticulum can be collectively referred to as the reticulorumen.

Figure 1:
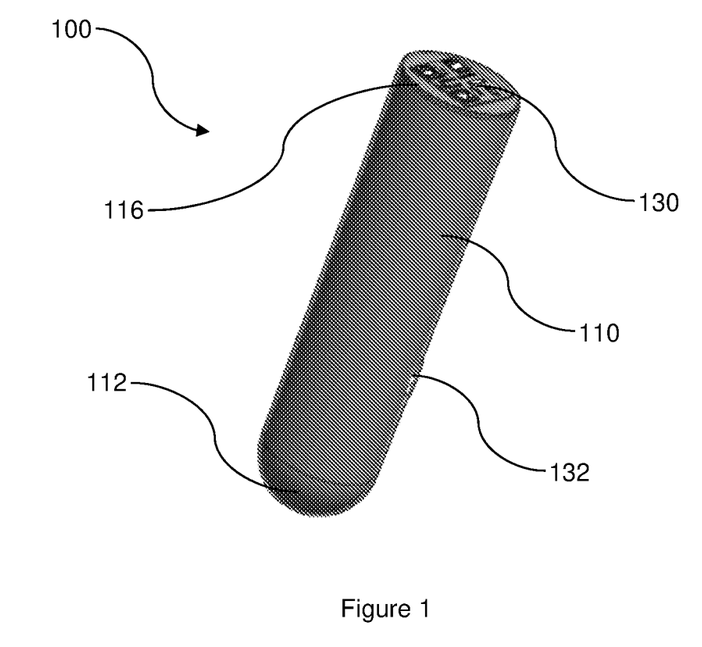
FIG. 1 is an illustration of an exterior of a monitoring device according to embodiments of the present disclosure.
Figure 2:
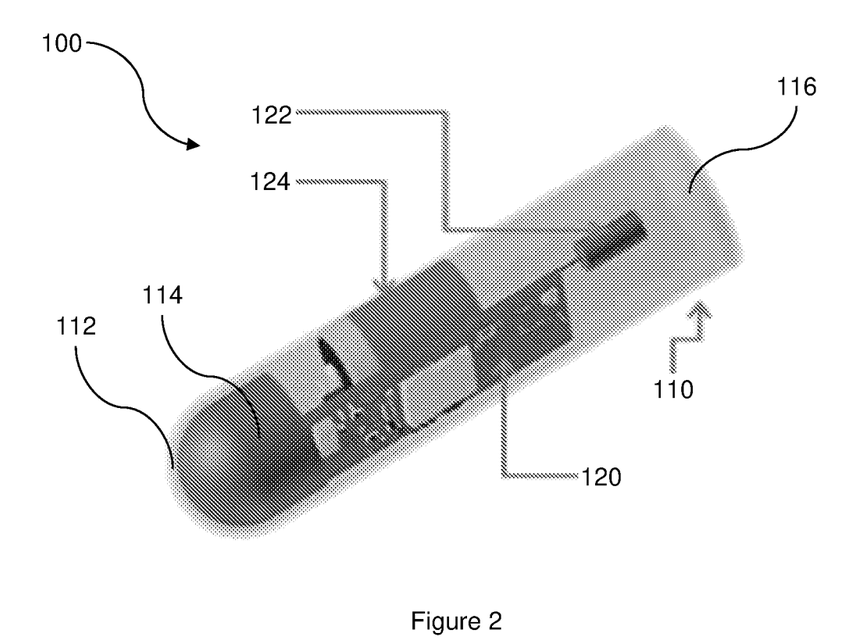
FIG. 2 is an illustration of an interior of the monitoring device.

In representative or exemplary embodiments of the present disclosure, with reference to FIG. 1 and FIG. 2, there is a monitoring device 100 for remotely monitoring health of a livestock animal. The livestock animal can an adult or a young and can be a ruminant. In many embodiments, the monitoring device 100 is used for remotely monitoring health of a young livestock animal, such as a young ruminant like a calf.

The monitoring device 100 includes an elongated body 110 that is within predefined dimensional limits. The predefined dimensional limits enable the monitoring device 100 to be orally administrable into the young livestock animal and to remain inside its stomach without being excreted. More specifically, the monitoring device 100 is small enough so that the monitoring device 100 can be orally administered, i.e. from the mouth through the oesophagus and into the stomach of the young livestock animal which is smaller than an adult one. If the monitoring device 100 is small enough for the young livestock animal, it would be orally administrable into an adult livestock animal. Further, the monitoring device 100 is large enough so that the monitoring device 100 stays inside its stomach and does not get excreted naturally. This allows the monitoring device 100 to be used for long term monitoring of the health of the young livestock animal.

Figure 3:
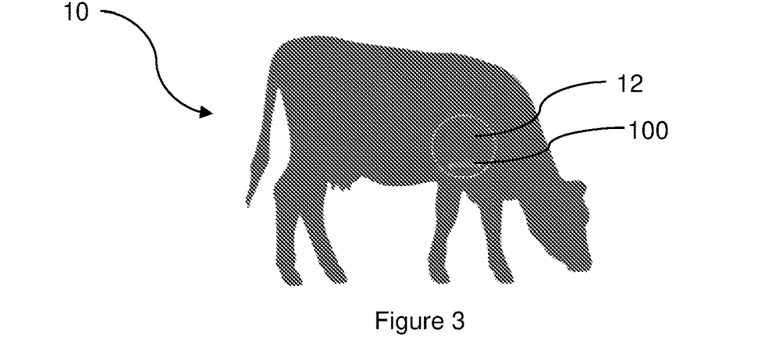
FIG. 3 is an illustration of a livestock animal having the monitoring device residing inside its stomach.

FIG. 3 illustrates an example of a livestock animal 10 having the monitoring device 100 residing in its stomach 12. The livestock animal 10 may be a ruminant, such as an adult cattle or young calf, and the monitoring device 100 resides in its reticulorumen. The monitoring device 100 may be referred to as a rumen bolus as it can reside in the rumen.

Based on the predefined dimensional limits, the elongated body 110 may have an overall width of up to 25±0.5 mm, and preferably up to 24±0.5 mm. Lengthwise, the elongated body 110 may have an overall length of up to 100±0.5 mm. The elongated body 110 may be tubular with an overall diameter of up to 25±0.5 mm, and preferably up to 24±0.5 mm. In some embodiments as shown in FIG. 1, the elongated body 110 includes a rounded front portion 112 to facilitate oral administration of the monitoring device 100 into the mouth of the livestock animal 10.

The elongated body 110 is made of a material that is non-toxic and safe for consumption as the monitoring device 100 would be residing in the stomach 12. The material is also resistant to aggressive/corrosive elements that are present in the stomach 12, such as acids and microbes that aid digestion, so that the monitoring device 100 can stay inside the stomach 12 without becoming severely damaged or being excreted out of the stomach 12 for a period of approximately up to 4 years.

As an example, the elongated body 110 may include a thermal epoxy material. As the monitoring device 100 is intended to remain entrenched in the stomach 12 for approximately up to 4 years, the electronic components are encapsulated in the elongated body 110 made of a special thermal epoxy material that protects the electronic components from being oxidized from heat generated in the stomach 12 and liquids in the stomach 12. Additionally, the elongated body 110 may be coated with a suitable material that is exposed to liquids in the stomach 12. Some non-limiting examples of the material are plastics approved by the United States Food and Drug Administration, such as food grade polypropylene. The polypropylene coating makes the monitoring device 100 safe to remain entrenched in the stomach 12 and the underlying thermal epoxy material protects electronic components from substances such as water vapour that may have permeated through the polypropylene coating over a long period of time.

The monitoring device 100 may include a ballast weight 114 housed within the elongated body 110 to increase the overall weight and density of the monitoring device 100. The ballast weight 114 may be made of a metallic material. The ballast weight 114 may be positioned closer to the front portion 112, so that the centre of mass of the monitoring device 100 is shifted towards the front portion 112. This arrangement front weights the monitoring device 100 to facilitate the oral administration. More specifically, the front weighting assists in directing travel of the monitoring device 100 through the oesophagus of the livestock animal 10, including a young one.

In one working prototype of the monitoring device 100, the elongated body 110 has a tubular profile with a rounded front portion 112, an overall length of 100 mm, and overall width of 25 mm. In another working prototype, the elongated body 110 has an overall length of 100 mm, and overall width of 24 mm.

The monitoring device 100 has an overall weight from approximately 85 to 95 g, preferably from approximately 87 to 89 g, and more preferably at approximately 88 g. Based on the dimensions of the monitoring device 100 as described above, the monitoring device 100 has an overall density from approximately 2.0 to 2.1 g/cm$^3$, preferably from approximately 2.03 to 2.08 g/cm$^3$, and more preferably at approximately 2.03 g/cm$^3$.

The overall size, weight, and density of the monitoring device 100, together with the front weighting of the monitoring device 100, enable the monitoring device 100 to remain lodged in the stomach 12 without being excreted out (for up to 4 years) and to ameliorate discomfort to the livestock animal 10. Moreover, at the preferred overall weight and density, the monitoring device 100 would be in a floated position inside the stomach 12, enabling higher gain for antenna reception (by a wireless communications component of the monitoring device 100), and minimizing unnecessary disruption for transmission of temperature data, as described further below. The front weighting by the ballast weight 114 lowers the centre of mass of the monitoring device 100 when it is lodged in the stomach 12, enabling the monitoring device 100 to float in a more upright position for optimal wireless communications.

The monitoring device 100 further includes a set of electronic components housed within the elongated body 110. More specifically, the electronic components are encased inside the elongated body 110 such that the monitoring deice 100 is tamperproof and the electronic components are not exposed to external elements. The elongated body 110 forms a shell casing over the electronic components and protects them against the aggressive/corrosive elements inside the animal's stomach 12. Preferably, the enclosure protection provided by the elongated body 110 meets the Ingress Protection Code 67 standard.

The electronic components include a temperature sensor for measuring body temperature of the livestock animal 10. More specifically, as the monitoring device 100 will reside in the animal's stomach 12, the temperature sensor measures, within an accuracy of ±0.2° C., the internal body temperature of the stomach 12. It will be appreciated that various types of temperature sensor can be used, as will be readily understood by the skilled person. The electronic components may include other sensors to measure other physiological parameters of the livestock animal 10. Some non-limiting examples of such other sensors are pH sensors to measure the pH values (i.e. acidity/alkalinity) of liquids inside the stomach 12. The pH values can be used to identify the onset flatulence or bloating in the stomach 12 so that such conditions can be quickly remedied to improve the health of the livestock animal 10.

The electronic components further include a computer processor for processing the measured temperature into temperature data, and a wireless communications component for transmitting the temperature data to a remote computer device. More specifically, the temperature sensor measures the raw temperature values of the animal's internal body temperature. The computer processor receives the temperature values from the temperature sensor and processes them into electronic temperature data for onward transmission by the wireless communications component. As the monitoring device 100 is inside the animal's stomach 12, the wireless communications component transmits the temperature data using suitable wireless communication protocols, preferably for long range communications, as will be described further below. The remote computer device is configured for receiving and processing the temperature data to monitor the health of the livestock animals 10.

The computer processor may be configured for controlling the temperature sensor and wireless communications component to perform measuring of the body temperature at predefined intervals and transmitting the temperature data at predefined intervals. For example, the temperature sensor is configured to measure the body temperature at 15-minute intervals, while the wireless communications component is configured to transmit the temperature data at 30-minute intervals. The computer processor may be configured to adjust the measurement and transmission intervals as desired, such as based on instructions received from the remote computer device.

The temperature sensor, computer processor, and wireless communications component may be integrated together in a printed circuit board assembly (PCBA) 120. The electronic components may further include an antenna component 122 for boosting the wireless transmissions to the remote computer device. The antenna component 122 may be integrated in the PCBA 120 or separately connected to the PCBA 120.

The electronic components further include a battery 124 for powering the electronic components. The battery 124 is separately connected to the PCBA 120 and is designed with a unique battery management capability such that the battery 124 has a battery lifespan of approximately up to 4 years. This means the monitoring device 100 can continue measuring the body temperature and transmit the temperature data for approximately up to 4 years. Additionally, the elongated body 110 encasing the battery 124 also seals any chemical leakages from the 124 within the elongate body 110, thereby protecting the livestock animal 10 from such chemical leakages.

In some embodiments, the electronic components optionally include a data storage or memory component connected to the computer processor for storing the temperature data. The memory component has a capacity to store a predefined number of temperature data. For example, the memory component can store 16 temperature values measured at 15-minute intervals, equivalent to approximately 4 hours of temperature data. The memory component serves as a backup storage in case the monitoring device 100 is out of range of the remote computer device, particularly if the livestock animal 10 has wandered too far away. The temperature data that has not been transmitted, as well as new temperature data that has been processed during the period when the monitoring device 100 was out of range, would be transmitted to the remote computer device when the monitoring device 100 returns to communication range.

In some embodiments, the electronic components optionally include an electronic identification device to enable electronic identification of the particular livestock. For example, the identification device is a short range identification device or transponder such as a RFID (radio frequency identification) device or a NFC (near field communication) device. The livestock animal 10 having the monitoring device 100 residing inside its stomach 12 may be identified when it passes through a gantry or gate reader that detects the identification device. Regulatory bodies in many European countries mandate the use of RFID devices or transponders for identification of livestock animals 10. By incorporating the RFID device or transponder in the monitoring device 100 residing in the animal's stomach 12, the RFID device or transponder can be detected when the livestock animal 10 passes through the gantry or gate reader, thereby identifying and registering the livestock animal 10.

To enable wireless communications between the monitoring device 100 and the remote computer device, the monitoring device 100 first needs to be paired with the remote computer device. The monitoring device 100 is pre-programmed or predefined with a set of identification data or credentials, such as including a network address for use in communications within a network centred at the remote computer device. One example of the network address is a media access control (MAC) address.

Depending on the wireless communication protocol, the predefined identification data or device credentials may include those that are unique to the protocol, such as a low-power wide-area network protocol. An example of such protocol is LoRa which may employ the LoRaWAN® network architecture and specification. The LoRaWAN® specification describes certain device credentials that should be predefined for the monitoring device 100. The device credentials in the LoRaWAN® specification may include DevEUI, JoinEUI, and AppKey, as will be readily understood by the skilled person.

Figure 4:
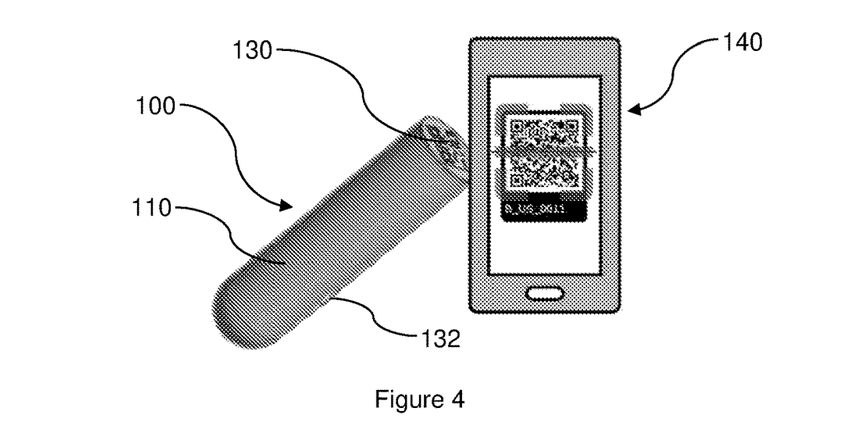
FIG. 4 is an illustration of the monitoring device comprising a data matrix code.

In one embodiment, the predefined identification data for the monitoring device 100 is provided by the manufacturer in printed form, such as in the operations manual. In another embodiment, the manufacturer provides a link to a secured website for retrieval of the predefined identification data. In another embodiment and as shown in FIG. 4, the monitoring device 100 includes a data matrix code 130 for retrieving the predefined identification data. The data matrix code 130 may be in the form of a QR code disposed at a rear portion 116 of the elongated body 110. The data matrix code 130 may be integrally formed or embedded, such as by direct printing, on the rear portion 116. Alternatively, the data matrix code 130 is visible on a label or sticker, such as by printing thereon, that is detachably attached to the rear portion 116.

The predefined identification data can be retrieved by using an electronic device 140, such as a mobile phone or tablet device having a camera, to scan the data matrix code 130. In one example, the predefined identification data is encoded in the data matrix code 130 and retrieved in response in response to the scan. In another example, an online address link is encoded in the data matrix code 130 and the electronic device 140 is directed to the online address, such as the secured website mentioned above, for retrieval of the predefined identification data. The retrieved predefined identification data or device credentials may subsequently be used for pairing and registration of the monitoring device 100 with the remote computer device. For example, the device credentials are entered into the remote computer device for it to identify and pair with the monitoring device 100.

The monitoring device 100 is initially in an inactive or standby mode wherein the power consumption from the battery 124 is minimal. In the inactive mode, the monitoring device 100 does not measure any temperature nor transmit any temperature data. Before orally administering the monitoring device 100 into the livestock animal 10, the monitoring device 100 needs to be activated to the active mode.

Figure 5:
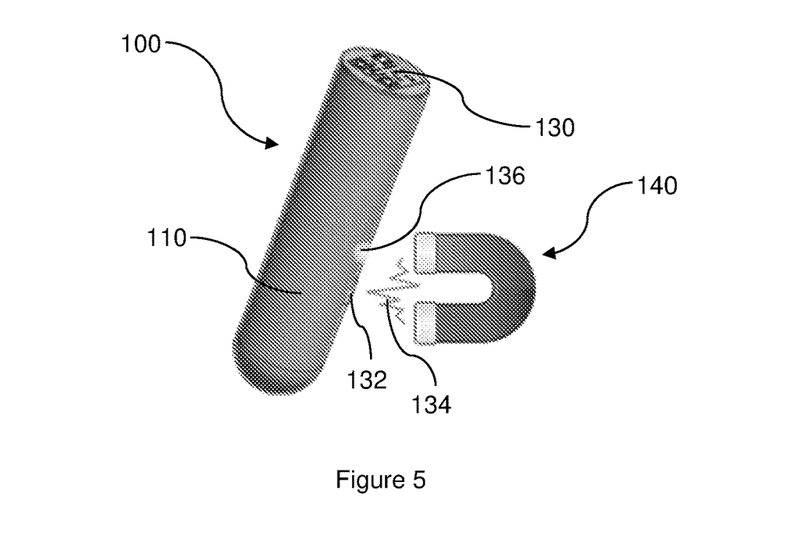
FIG. 5 is an illustration of the monitoring device being activated using an external magnetic device.

The monitoring device 100 may include a magnetic mechanism 132 housed within the elongated body 110 and configured for activating the monitoring device 100. Like the electronic components, the magnetic mechanism 132 is encased inside and shielded by the elongated body 110, and is operative by a magnetic field. More specifically, as shown in FIG. 5, an external magnetic device 142 is placed near the magnetic mechanism 132. The external magnetic device 142 generates a magnetic field and causes magnetic interference 134 with the magnetic mechanism 132. The monitoring device 100 is activated in response to the magnetic mechanism 132 detecting the magnetic interference 134. A detachable label or sticker may be placed on the surface of the elongated body 110 to locate the magnetic mechanism 132 housed therein.

As shown in FIG. 5, the monitoring device 100 may include a lighting element 136, such as including a light emitting diode (LED) housed within the elongated body 110. Like the electronic components, the magnetic mechanism 132 is encased inside and shielded by the elongated body 110. The elongated body 110 may include a transparent/translucent area so that light signals generated by the inside lighting element 136 can be seen. The lighting element 136 is configured for visual indication of activation of the monitoring device 100. For example, the lighting element 136 may generate a light signal (such as by flashing a number of times, e.g. 5) in response to successful activation of the monitoring device 100. The lighting element 136 may generate a different light signal if the activation fails.

Upon activation of the monitoring device 100, the monitoring device 100 attempts to join or register with the remote computer device and transmits an activation data packet to the remote computer device. The activation data packet includes the predefined identification data or device credentials of the monitoring device 100. The remote computer device receives the activation data packet and matches the device credentials. If the device credentials match those that has been entered into the remote computer device, the monitoring device 100 is successfully paired and registered with the remote computer device. The lighting element 136 may generate another light signal (such as by flashing a number of times, e.g. 5) in response to successful registration of the monitoring device 100 with the remote computer device. The flashes in the light signals for successful activation and successful registration may be at different frequencies to differentiate the light signals. The lighting element 136 may generate a different light signal if the registration fails.

The registration may fail due to various possible reasons, such as if the device credentials were incorrectly entered into the remote computer device or if the monitoring device 100 is out of range. The monitoring device 100 may be configured for a reset to the inactive mode before reattempting registration with the remote computer device.

In one embodiment, the reset can be performed by placing the external magnetic device 142 near the magnetic mechanism 132. The reset is initiated in response to the magnetic mechanism 132 detecting the magnetic interference 134. The lighting element 136 may generate a light signal (such as by flashing a number of times, e.g. 3) in response to successful reset of the monitoring device 100. The monitoring device 100 reverts to the inactive mode after the successful reset. Repeating the steps described above, the external magnetic device 142 can be used to activate the monitoring device 100 and reattempt registration with the remote computer device.

Upon successful registration of the monitoring device 100 with the remote computer device, wireless communications between the monitoring device 100 and the remote computer device is enabled. The monitoring device 100 begins to measure temperature and transmit temperature data to the remote computer device according to the predefined intervals. The lighting element 136 may generate a light signal (such as by flashing once) every time the temperature data is transmitted. Additionally, the monitoring device 100 may be configured to disable the magnetic mechanism 132 so that the monitoring device 100 cannot be reset anymore. This would mean that the monitoring device 100 is permanently paired with the remote computer device.

Figure 6:
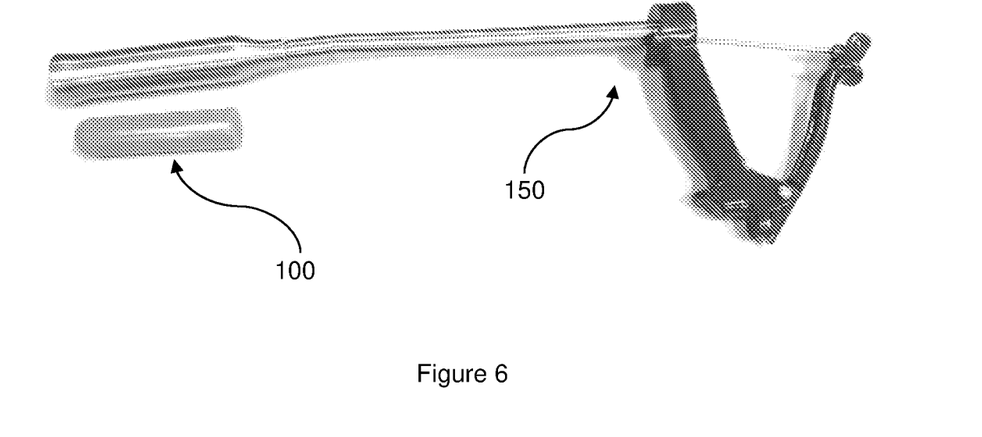
FIG. 6 is an illustration of a rumen bolus applicator for inserting the monitoring device into the livestock animal.

After successfully activation and registration of the monitoring device 100, the monitoring device 100 needs to be orally administered into the livestock animal 10. For example, as shown in FIG. 6, a rumen bolus applicator 150 can be used to insert the monitoring device 100, which is in the form of a rumen bolus, into the livestock animal 10. As described above, the monitoring device 100 is sized to fit in the oesophagus of the livestock animal 10, including a young ruminant, and sit in the stomach 12 (e.g. reticulorumen) without being excreted.

In some embodiments, the monitoring device 100 has detachable labels or stickers on the elongated body 110, such as to show the data matrix code 130 and locate the magnetic mechanism 132. These labels should be detached from the monitoring device 100 before orally administering the monitoring device 100, as the labels may contain contaminants potentially harmful to the livestock animal 10.

The monitoring device 100 may include a human-readable identifier integrally formed on the elongated body 110. This human-readable identifier provides a means for identifying the monitoring device 100 among a large number of monitoring devices 100, since a farm has a large number of livestock animals 10. The human-readable identifier may be a string of text characters, such as numbers that number the monitoring devices 100 sequentially. The human-readable identifier may be integrally formed on any part of the elongated body 110, such as on the rear portion 116 so that the monitoring device 100 can be identified after the label containing the data matrix code 130 is removed. The human-readable identifier may be integrally formed using various means such as laser printing and engraving.

Figure 7:
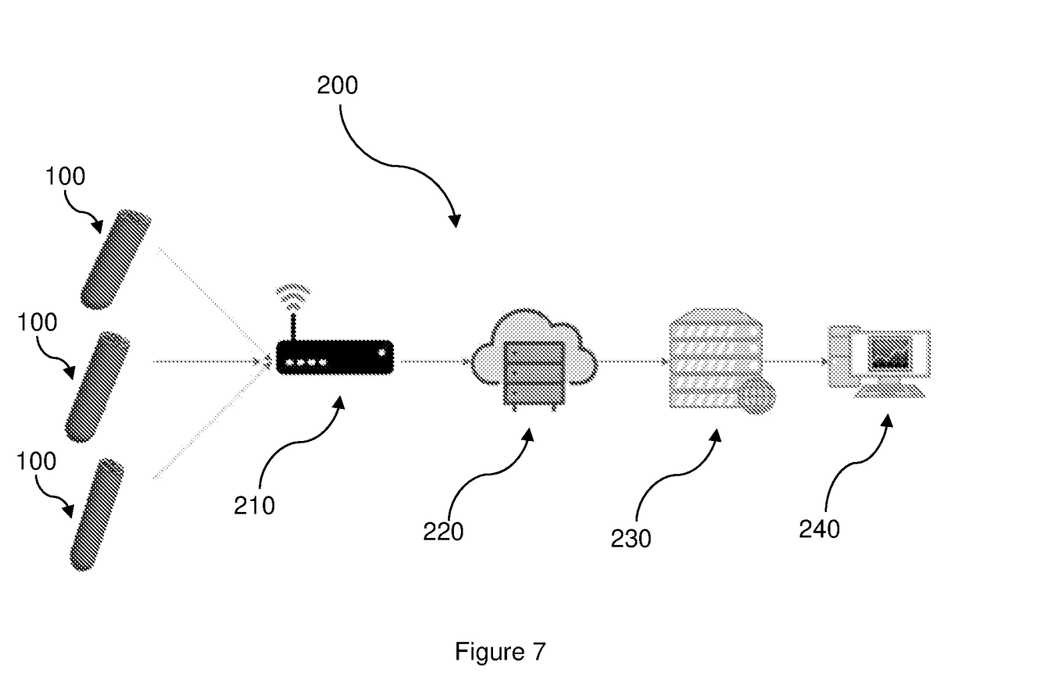
FIG. 7 is an illustration of a monitoring system comprising a set of the monitoring devices.

In representative or exemplary embodiments of the present disclosure, with reference to FIG. 7, there is a monitoring system 200 for remotely monitoring health of livestock animals 10 including young livestock animals. The monitoring system 200 includes a set of one or more monitoring devices 100 and the remote computer device communicative with the monitoring devices 100. Each monitoring device 100 resides in the stomach 12 of a respective livestock animal 10 and has the elongated body 110 within the predefined dimensional limits such that the monitoring device 100 is orally administered into the livestock animal 10 (even a young one) and remains inside the stomach 12 without being excreted.

In many embodiments, the communication between the monitoring devices 100 and the remote computer device is based on the LoRa wireless communication protocol which employs the LoRaWAN® specification. The LoRaWAN® protocol enables data transmissions at low power and over long distances up to a few kilometres, making it suitable for use in livestock farms that span across large areas of land. Additionally, the LoRaWAN® protocol has a large network capacity for the network of monitoring devices 100, making it suitable for use with large numbers of livestock animals 10 on the farm.

The remote computer device in the monitoring system 200 may be referred to as a gateway server 210 that communicates with the network of monitoring devices 100. The gateway server 210 manages secure gateway connections with and configurations of the monitoring devices 100.

The monitoring system 200 further includes a network server 220 that implements the LoRaWAN® protocol and is communicative with the gateway server 210. The network server 220 is configured for validating the authenticity of the monitoring devices 100 and authenticating the data received from the monitoring devices 100 via the gateway server 210. More specifically, the gateway server 210 receives the temperature data at predefined intervals from each respective monitoring device 100, and transmits the temperature data to the network server 220.

The monitoring system 200 further includes an application server 230 communicative with the network server 220. The application server 230 is configured for decrypting the data received from the network server 220 and encrypting the data transmitted to the network server 220. More specifically, the gateway server 210 forwards the temperature data from the monitoring devices 100 to the network server 220, which then authenticates the temperature data and forwards it to the application server 230. The application server 230 then decrypts and processes the temperature data.

The monitoring system 200 may further include an online dashboard or interface 240 for viewing the processed temperature data. The online interface 240 may include various functionalities such as data analytics to analyse the temperature data and evaluate the health of the livestock animals 10. Suitable machine learning algorithms may be implemented and trained with a temperature dataset to determine various health conditions of the livestock animals 10, such as fever or onset of diseases.

Some non-limiting examples of the gateway server 210, network server 220, and application server 230 include computers, laptops, mini-computers, mainframe computers, any non-transient and tangible machines that can execute a machine-readable code, cloud-based servers, distributed server networks, and a network of computer systems. As used herein, a server is a physical or cloud data processing system on which a server program runs. The server may be implemented in hardware or software, or a combination thereof. Additionally, the gateway server 210, network server 220, and application server 230 each includes a processor, a memory, and various other modules or components. The modules and components thereof are configured for performing various operations or steps and are configured as part of the processor. Such operations or steps are performed in response to non-transitory instructions operative or executed by the processor. The memory is used to store instructions and perhaps data which are read during program execution. The memory may be referred to in some contexts as computer-readable storage media and/or non-transitory computer-readable media. Non-transitory computer-readable media include all computer-readable media, with the sole exception being a transitory propagating signal per se.

Each monitoring device 100 can thus monitor the body temperature of a respective livestock animal 10 remotely and passively, as the monitoring device 100 is orally administered into the livestock animal 10 and resides in the stomach 12 without being excreted. The size of the monitoring device 100 makes it suitable for oral administration into small young livestock animals 10, even those as young as 2 weeks old. For ruminants, the body temperature may be referred to as the intraruminal temperature as it is measured inside the rumen. Notably, the intraruminal temperature is independent of external factors and cannot be manipulated from the outside, but it is usually 0.5° C. higher than the core body temperature due to the activity of heat-producing microbes in the rumen.

The monitoring system 200 can be implemented with any LoRaWAN® network and the monitoring device 100 measures the body temperature and sends the temperature data to the gateway server 210. The temperature data is subsequently processed and can be monitored on the online interface 240. The monitoring device 100 obviates the need for manual measuring of body temperature, which is labour-intensive, and enables real-time remote monitoring of the body temperature.

Monitoring of the body temperature is one of the most effective ways of evaluating the health of livestock animals 10. Farms can more accurately assesses and predict good health of livestock animals 10 based on their body temperature. Real-time monitoring of the animal's health aids in the early detection of diseases. This allows the farm workers to quickly respond to any possible occurrence of diseases and treat the livestock animal 10 accordingly. Early treatment of livestock animals 10 reduces their mortality rate and thereby increase the livestock farm's productivity which dependent on their health. Labour costs for the farm can also be reduced as less manpower is needed to operate the monitoring system 200 and the monitoring devices 100, as opposed to manual measurements using thermometers.

The normal body temperature range for a livestock animal 10 may differ depending on various factors, such as species, gender, and age. For example, the normal body temperature may range from 38.3 to 38.8° C. for adult cattle, and from 38.5 to 39.5° C. for young calves. Whenever the livestock animal 10 consumes water, the temperature would drop a little. Thus, the temperature data can be monitored to determine whether the livestock animal 10 is consuming water at appropriate intervals. If the livestock animal 10 is found to have not been consuming water for an extended time period, farm workers may intervene by moving it to a water source or investigate for suspicious health deficiency.

If the livestock animal 10 is not consuming enough water, or if the temperature data shows the body temperature deviating from the normal range, the farm workers may take preventive measures to improve the health of the livestock animal 10. For example, the farm workers can adequately prescribe the right intervention, such as hydrating the livestock animal 10 and feeding nutritious animal feed to ensure optimal health is maintained.

If the temperature data shows the body temperature constantly above the normal range, then this could mean that the livestock animal 10 is febrile, which usually indicates an infection or disease. The health condition of the livestock animal 10 should be evaluated further, such as by determining whether the livestock animal 10 has other symptoms like lethargy and lack of appetite. Farm workers can then promptly prescribe the right resources to treat the livestock animal 10 before the health condition worsens, such as by administering medication (e.g. antibiotics), and/or health supplements (e.g. vitamins). The livestock animal 10 should also be isolated to prevent spread or outbreak of any infection or disease to other livestock animals 10. This could help the farm save costs as any potential losses from such infection or disease would be limited to only one or a few livestock animals 10.

If the livestock animal 10 is female, elevations in the body temperature could indicate that the livestock animal is on heat, meaning that the female livestock animal 10 is in oestrus which is the receptive period of the sexual cycle. Suitable measures should then be taken for the female livestock animal 10 to mate with a male livestock animal 10. Moreover, by deliberating pairing certain species of male and female livestock animals 10 for mating, the farm breed certain species of livestock and increase their population, especially those that are commercially valuable to the farm.

As the monitoring device 100 can be used in young livestock animals 10, monitoring their body temperature can reduce rate of premature deaths that could happen due to infection or disease, especially since young livestock animals 10 have weaker immunity. The young livestock animals 10 can continue to grow healthily into adults before they are processed, e.g. culled, for sale. Notably, adult livestock is often more valuable than young livestock as adult livestock is heavier and can yield more meat. With lower mortality rates, a greater number of healthy livestock animals 10 can be processed for sale, thus increasing revenue for the farm.

Additionally, the monitoring system 200 implements LoRaWAN® protocol which provides for long range communication and a large network capacity. A large number of monitoring devices 100 can thus be connected to a single gateway server 210. This significantly reduces the costs of deploying multiple gateway servers 210 and the manpower needed to operate and maintain them. Farms can manage their farm resources more appropriately by deploying the right resources in a timely manner, and as and when required. Thus, use of the monitoring devices 100 and the monitoring system 200 can help reduce operating costs, as well as increase productivity and revenue stream for the farms.

In the foregoing detailed description, embodiments of the present disclosure in relation to a monitoring system and device for livestock are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

The invention claimed is:

1. A monitoring device for remotely monitoring health of a livestock animal, the monitoring device comprising:
    an elongated body within predefined dimensional limits that enable the monitoring device to be orally administrable into the livestock animal and to remain inside its stomach without being excreted;
    a set of electronic components housed within the elongated body, the electronic components comprising:
        a battery for powering the electronic components;
        a temperature sensor for measuring body temperature of the livestock animal;
        a computer processor for processing the measured temperature into temperature data; and
        a wireless communications component for transmitting the temperature data to a remote computer device for processing to monitor the health of the livestock animal; and
    a magnetic mechanism housed within the elongated body and configured for:
        activating the monitoring device in response to the magnetic mechanism detecting magnetic interference from an external magnetic device; and
        registering the monitoring device with the remote computer device to thereby pair the monitoring device with the remote computer device, said registration comprises transmitting, in response to said activation of the monitoring device, an activation data packet to the remote computer device for matching with predefined identification data of the monitoring device, wherein the magnetic mechanism is configured for resetting the monitoring device to an inactive mode in order to reattempt registration with the remote computer device; and wherein the monitoring device is configured to disable the magnetic mechanism after said registration to prevent resetting of the monitoring device, thereby permanently pairing the monitoring device with the remote computer device.

2. The monitoring device according to claim 1, wherein the elongated body has an overall width of up to 25 mm, wherein the elongated body has an overall length of up to 100 mm, and/or wherein the monitoring device has an overall weight from 85 g to 95 g.

3. The monitoring device according to claim 1, wherein the elongated body is tubular and comprises a rounded front portion to facilitate oral administration of the monitoring device.

4. The monitoring device according to claim 1, wherein the monitoring device is front weighted to facilitate oral administration of the monitoring device.

5. The monitoring device according to claim 1, wherein the electronic components further comprise a memory component connected to the computer processor for storing the temperature data.

6. The monitoring device according to claim 1, wherein the wireless communications component is configured for transmission using a LoRa wireless communication protocol.

7. The monitoring device according to claim 1, wherein the computer processor is configured for controlling the temperature sensor and wireless communications component to perform said measuring and transmitting at predefined intervals.

8. The monitoring device according to claim 1, wherein said reset is performed in response to the magnetic mechanism detecting magnetic interference from the external magnetic device.

9. The monitoring device according to claim 8, further comprising a lighting element housed within the elongated body and configured for visual indication of activation of the monitoring device.

10. The monitoring device according to claim 1, further comprising a data matrix code for retrieving the predefined identification data of the monitoring device.

11. The monitoring device according to claim 10, further comprising a detachable label attached on the elongated body, wherein the data matrix code is visible on the label.

12. The monitoring device according to claim 1, further comprising a human-readable identifier of the monitoring device integrally formed on the elongated body.

13. The monitoring device according to claim 1, wherein the elongated body comprises a thermal epoxy material, and/or wherein the elongated body is coated with a food grade polypropylene material.

14. The monitoring device according to claim 1, wherein the electronic components further comprise a RFID transponder to enable electronic identification of the livestock animal.

15. A monitoring system for remotely monitoring health of livestock animals, the monitoring system comprising:

a set of monitoring devices;

a remote computer device communicative with the monitoring devices; and each monitoring device residing in a stomach of a respective livestock animal, the monitoring device comprising:

an elongated body within predefined dimensional limits that enable the monitoring device to be orally administrable into the livestock animal to remain inside its stomach without being excreted;

a set of electronic components housed within the elongated body, the electronic components comprising:

a battery for powering the electronic components;

a temperature sensor for measuring temperature of the livestock animal;

a computer processor for processing the measured temperatures into temperature data; and a wireless communications component for transmitting the temperature data to the remote computer device; and a magnetic mechanism housed within the elongated body and configured for:

activating the monitoring device in response to the magnetic mechanism detecting magnetic interference from an external magnetic device; and registering the monitoring device with the remote computer device, said registration comprises transmitting, in response to said activation of the monitoring device, an activation data packet to the remote computer device for matching with predefined identification data of the monitoring device, wherein the magnetic mechanism is configured for resetting the monitoring device to an inactive mode in order to reattempt registration with the remote computer device; and wherein the monitoring device is configured to disable the magnetic mechanism after said registration to prevent resetting of the monitoring device, thereby permanently pairing the monitoring device with the remote computer device, wherein the remote computer device is configured for processing the temperature data to monitor the health of the livestock animals.

16. The monitoring system according to claim 15, wherein communication between the monitoring devices and the remote computer device is based on the LoRa wireless communication protocol.

17. The monitoring system according to claim 15, wherein said reset is performed in response to the magnetic mechanism detecting magnetic interference from the external magnetic device.

* * * * *